(12) United States Patent
Crawford et al.

(10) Patent No.: US 11,576,798 B2
(45) Date of Patent: Feb. 14, 2023

(54) STENTS AND METHODS FOR MANAGING PASSAGE OF MATERIAL THROUGH A BODY LUMEN

(71) Applicant: Boston Scientific Scimed, Inc., Maple Grove, MN (US)

(72) Inventors: Richard Crawford, Galway (IE); Louis McNern, Donegal (IE); Gary Gilmartin, Foxford (IE); Susanne O'Reilly, Dublin (IE)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 7 days.

(21) Appl. No.: 16/925,701

(22) Filed: Jul. 10, 2020

(65) Prior Publication Data

US 2021/0007869 A1    Jan. 14, 2021

Related U.S. Application Data

(60) Provisional application No. 62/873,241, filed on Jul. 12, 2019.

(51) Int. Cl.
*A61F 2/90* (2013.01)
*A61F 2/848* (2013.01)

(52) U.S. Cl.
CPC ............ *A61F 2/90* (2013.01); *A61F 2/848* (2013.01); *A61F 2002/8483* (2013.01); *A61F 2230/001* (2013.01); *A61F 2250/0039* (2013.01)

(58) Field of Classification Search
None
See application file for complete search history.

(56) References Cited

U.S. PATENT DOCUMENTS

| 5,197,984 A * | 3/1993 | Kedem ............... A61F 2/0009 604/351 |
| 6,641,573 B1 * | 11/2003 | Parodi ............... A61M 25/10 604/510 |
| 8,414,635 B2 | 4/2013 | Hyodoh et al. |
| 9,592,139 B2 | 3/2017 | Davidson et al. |

(Continued)

FOREIGN PATENT DOCUMENTS

| WO | 2018232026 A1 | 12/2018 |
| WO | 2020023514 A1 | 1/2020 |

OTHER PUBLICATIONS

International Search Report and Written Opinion for the International Patent Application No. PCT/US2020/041538, dated Sep. 25, 2020, 12 pages.

*Primary Examiner* — Leslie Lopez
(74) *Attorney, Agent, or Firm* — Seager, Tufte & Wickhem, LLP (57) ABSTRACT

The present disclosure relates generally to stents and methods for managing passage of material through a body lumen. In some embodiments, a medical stent may include a stent body defined by a hollow tubular elongate structure extending along a central axis, the stent body including a first portion and a second portion. The medical stent may further include a control region between the first and second portions, wherein in a first configuration the hollow tubular elongate structure of the control region is in a closed, twisted configuration, and wherein in a second configuration the hollow tubular elongate structure of the control region is in an open, expanded configuration.

20 Claims, 6 Drawing Sheets

(56) References Cited

U.S. PATENT DOCUMENTS

| | | |
|---|---|---|
| 10,420,665 B2 | 9/2019 | Sharma et al. |
| 2003/0153935 A1* | 8/2003 | Mialhe ............. A61B 17/12022 623/1.15 |
| 2010/0036504 A1* | 2/2010 | Sobrino-Serrano ....... A61F 2/90 623/23.68 |
| 2011/0306916 A1* | 12/2011 | Nitzan ................ A61M 27/006 604/9 |
| 2015/0100113 A1 | 4/2015 | Davidson et al. |
| 2015/0142049 A1* | 5/2015 | Delgado ............ A61B 17/3468 606/216 |
| 2015/0313603 A1* | 11/2015 | Bödewadt ........ A61B 17/12109 606/191 |
| 2015/0374383 A1* | 12/2015 | Bödewadt ........ A61B 17/12145 606/157 |
| 2017/0367711 A1 | 12/2017 | Bödewadt et al. |
| 2019/0298559 A1 | 10/2019 | Gupta et al. |

* cited by examiner

STENTS AND METHODS FOR MANAGING PASSAGE OF MATERIAL THROUGH A BODY LUMEN

CROSS-REFERENCE TO RELATED APPLICATIONS

The present application claims the benefit of priority under 35 U.S.C. § 119 to U.S. Provisional Patent Application 62/873,241, filed Jul. 12, 2019, which application is incorporated herein by reference in its entirety for all purposes.

FIELD

The present disclosure relates to medical stents and, more particularly, to stents and methods for managing passage of material through a body lumen.

BACKGROUND

Sphincter muscles in the human anatomy perform an important role of sealing and preventing leaks from organs and vessels. Examples of sphincters in the body include a lower esophageal sphincter (LES) and internal/external anal sphincters (IAS/EAS). Complications that effect sphincter function can cause discomfort and embarrassment, thus impairing a patient's quality of life.

One example of sphincter dysfunction, fecal incontinence, is recognized as the inability to control bowel movements, causing unexpected rectum leakage of stool. A challenge for people with this condition is the lack of notification of the imminent bowel movement. Due to the lack of a natural, physical urge or alert to the bowel movement, some people with the condition resort to wearing absorbent undergarments. However, this solution fails to prevent unintentional stool leakage before it occurs.

Urinary incontinence is a dysfunction that may occur, for example, during and/or after pregnancy. This unintentional leaking of urine may present a level of discomfort for patients, which may lead to self-esteem and self-confidence issues.

Gastroesophageal reflux disease (GERD) is a dysfunction that occurs when the stomach contents can pass the LES, due to muscle weakness and/or inappropriate relaxation. GELD can also be a complication from surgical procedures that effect the sphincter muscle, e.g., peroral endoscopic myotomy (POEM) and Heller myotomy procedures to treat achalasia.

SUMMARY

The present disclosure in its various embodiments relates generally to stents and methods for managing sphincter dysfunction. In one or more embodiments, a medical stent may include a stent body defined by a hollow tubular elongate structure extending along a central axis, the stent body including a first portion and a second portion. The medical stent may further include a control region between the first and second portions, wherein in a first configuration the hollow tubular elongate structure of the control region is in a closed, twisted configuration, and wherein in a second configuration the hollow tubular elongate structure of the control region is in an open, expanded configuration. In some embodiments, the control region may be connected at a first end to the first portion and at a second end to the second portion. In some embodiments, the medical stent may further include a covering formed along the hollow tubular elongate structure. In some embodiments, the covering may be made from silicone. In some embodiments, in the first configuration, the second portion may be rotated more than 180 degrees relative to the first portion. In some embodiments, in the first configuration the hollow tubular elongate structure of the control region is rotated about the central axis by approximately 360 degrees. In some embodiments, the control region may include a first constriction point. In some embodiments, the control region may include a second constriction point adjacent the first constriction point, wherein the hollow tubular elongate structure at each of the first and second constriction points is substantially closed. In some embodiments, at the first constriction point, the hollow tubular elongate structure of the control region may be rotated in a first direction about the central axis by 180 degrees, and at the second constriction point, the hollow tubular elongate structure of the control region may be rotated in a second direction about the central axis by 180 degrees. In some embodiments, the stent body may further include a lumen anchoring flange extending from at least one of: the first portion, and the second portion.

In one or more embodiments, a self-expanding metal stent may include a stent body defined by a hollow tubular elongate structure extending along a central axis, the stent body including a first portion adjacent a second portion. The stent body may further include a lumen anchoring flange extending from at least one of: the first portion, and the second portion. The self-expanding metal stent may further include a control region between the first portion and the second portion, wherein in a first configuration the hollow tubular elongate structure of the control region is twisted about the central axis to form a barrier within the stent body, and wherein in a second configuration the hollow tubular elongate structure of the control region is untwisted to provide a passageway between the first portion and the second portion. In some embodiments, the first portion includes a first open end and the second portion includes a second open end. In some embodiments, the self-expanding metal stent may further include a covering formed along the hollow tubular elongate structure. In some embodiments, in the second configuration, the second portion is rotated at least 180 degrees relative to the first section. In some embodiments, the barrier is formed at a first constriction point in the control region. In some embodiments, the hollow tubular elongate structure may include a second constriction point in the control region, wherein the hollow tubular elongate structure at the first constriction point is rotated about the central axis in a first direction, and wherein the hollow tubular elongate structure at the second constriction point is rotated about the central axis in a second direction.

In one or more embodiments, a method may include inserting a stent body within a gastrointestinal tract of a patient, wherein the stent body comprises a hollow tubular elongate structure extending along a central axis, and wherein the stent body comprises a first portion adjacent a second portion. The method may further include providing a barrier between the first portion and the second portion by twisting, about the central axis, the hollow tubular elongate structure of a control region, wherein the barrier is operable to untwist in response to a force upon the hollow tubular elongate structure of the control region to provide a passageway between the first portion and the second portion. In some embodiments, the method may further include forming one or more constriction points in the hollow tubular elongate structure of the control region, and thermally treating the one or more constriction points. In some embodiments, the method may further include securing the stent body within the gastrointestinal tract using a lumen anchoring flange extending from at least one of: the first portion, and the second portion. In some embodiments, the method may further include forming a covering over the hollow tubular elongate structure.

Various one or more of the features summarized above may be interchanged, exchanged, combined or substituted with or for other features summarized above, for use in connection with the medical systems and methods summarized above, and with respect to the embodiments described in greater detail below and embodiments otherwise within the scope of the present disclosure.

BRIEF DESCRIPTION OF THE DRAWINGS

Non-limiting embodiments of the present disclosure are described by way of example with reference to the accompanying figures, which are not intended to be drawn to scale. In the figures, each identical or nearly identical component illustrated is typically represented by a single numeral. For purposes of clarity, not every component is labeled in every figure, nor is every component of each embodiment shown where illustration is not necessary to allow those of ordinary skill in the art to understand the disclosure. Furthermore, some of the figures include cross-sectional views in the form of "slices", or "near-sighted" cross-sectional views, omitting certain background lines or features otherwise visible in a "true" cross-sectional view, for illustrative clarity. In the figures.

DETAILED DESCRIPTION

The present disclosure is not limited to the particular embodiments described herein. The terminology used herein is for the purpose of describing particular embodiments only, and is not intended to be limiting beyond the scope of the appended claims. Unless otherwise defined, all technical terms used herein have the same meaning as commonly understood by one of ordinary skill in the art to which the disclosure belongs.

Embodiments herein are directed to self-expanding stents implantable within a patient's body, the stent functioning as a one-way valve for the controlled passage of material through a gastrointestinal (GI) tract of the patient. For example, the stent is configured to allow passage of stool or other material in one direction once enough pressure has built up to cause the stent to change from a closed, twisted configuration to an open, expanded configuration. In some embodiments, the stent includes a hollow tubular elongate structure extending along a central axis, the hollow tubular elongate structure including a first portion and a second portion. A control region is disposed between the first and second portions, wherein the control region may twist and untwist to regulate delivery of the stool through an interior of the stent.

As will be described in greater detail herein, the stent may be placed in the GI tract of a patient, such as in a descending colon, to control unintentional flow of loose stool through the rectum and anus. The patient may receive a prompt, via abdominal sensation, as back pressure from the stent increases, thus allowing the patient a period of time before the stent opens. The control region of the stent may then untwist, allowing the normal flow of stool therethrough. In some embodiments, the stent is flexible, generally conforming to the profile of the stool. As a result, the control region of the stent may expand only by an amount corresponding to dimensions of the stool, thus allowing the stool to pass through the stent in a controlled manner. Once the stool has passed through the stent, the control region may return to the closed, twisted configuration.

Although described primarily herein as an approach for treating fecal incontinence, embodiments herein are not limited in this context. For example, the stents and methods of the present disclosure can be used treat gastroesophageal reflux disease (GERD) and/or urinary incontinence, among other types of sphincter dysfunction.

Figure 1:
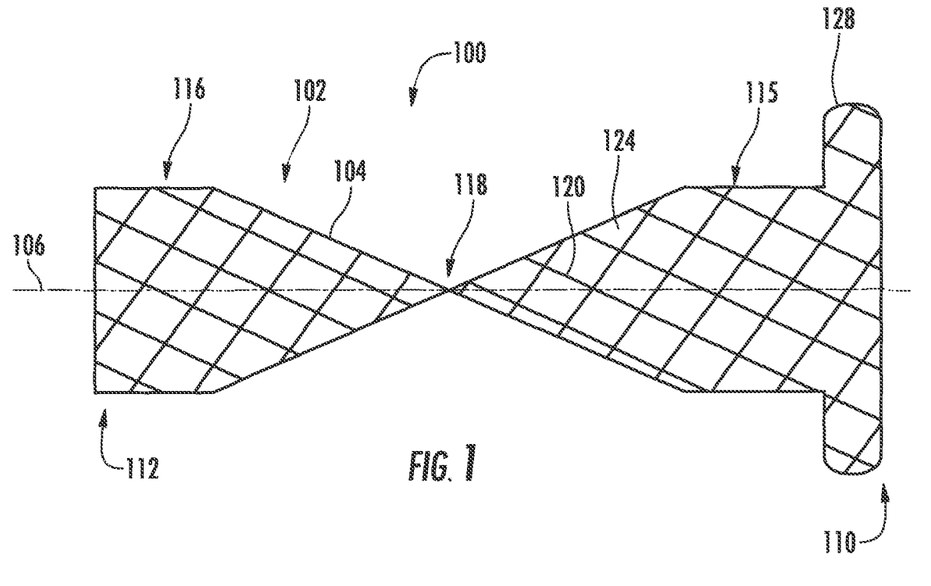
FIG. 1 is a side cross-sectional view of a stent according to embodiments of the present disclosure.

Turning now to FIG. 1, a stent 100 according to embodiments of the disclosure will be described in greater detail. As shown, the stent 100 may be a self-expanding metal stent (SEMS) positionable within a GI tract of a patient. The stent 100 may have a stent body 102 defined by a hollow tubular elongate structure 104 extending along a central axis 106, between a first end 110 and a second end 112. In some embodiments, each of the first end 110 and the second end 112 may be open ends to allow stool within the GI tract to enter and exit through the stent 100 in a controlled manner. As shown, the stent body 102 may include a first portion 115 and a second portion 116 connected to one another at a control region 118. In some embodiments, the hollow tubular elongate structure 104 may be formed of a hollow tubular elongate structure, although other embodiments may be formed at least partially of plastic, composite, metal, or combinations thereof. As will be described in greater detail below, the control region 118 may operate between a first configuration in which the hollow tubular elongate structure 104 of the control region 118 is in a closed, twisted form, and a second configuration in which the hollow tubular elongate structure 104 of the control region 118 is in an open, expanded form.

In some embodiments, the stent 100 may have a constant or non-constant diameter along the central axis 106. For example, as shown, the first portion 115 and the second portion 116 may narrow towards the control region 118. In some embodiments, a maximum diameter of the first portion 115 may be the same or different than a maximum diameter of the second portion 116. Furthermore, in various embodiments, a length of the first portion 115, as measured from the control region 118 to the first end 110, may be the same or different than a length of the second portion 116, as measured from the control region 118 to the second end 112. Embodiments herein are not limited in this context.

In some embodiments, the hollow tubular elongate structure 104 of the stent body 102 may include a plurality of frame members 120 surrounding an interior of the stent 100. As shown, the plurality of frame members 120 may be connected to one another to define a plurality of open cells 124 in the stent body 102. However, embodiments herein are not limited to any particular number of frame members 120 and/or configuration of the plurality of frame members 120 and the plurality of open cells 124. In embodiments, the stent body 102 may be formed of one or more wires in a predetermined weave pattern, thereby defining a plurality of interstices, or apertures in the weave pattern.

The plurality of frame members 120 may be made of an elastic material, such as shape-memory wire, stainless steel, nitinol, cobalt alloys, and/or other materials. Although non-limiting, the hollow tubular elongate structure 104 may be laser cut, woven, braided, bent, twisted, knotted, molded, tied, and/or wrapped from one or several filaments into a desired configuration. In some embodiments, the control region 118 may be twisted and then thermally treated to "heat-set" the hollow tubular elongate structure 104 into the configuration shown. In some embodiments, a thickness of one or more of the plurality of frame members 120 may vary as well. For example, a wire diameter in the control region 118 may vary relative other wire diameters of the hollow tubular elongate structure 104 in the first and/or second portions 115, 116 to alter a pressure threshold at which the hollow tubular elongate structure 104 of the control region 118 changes between the open and closed configurations.

The stent 100 may further include a covering 126 over at least a portion of the hollow tubular elongate structure 104. In non-limiting embodiments, the covering 126 may include one or more polymeric coatings, such as polytetrafluoroethylene (PTFE), expanded PTFE (ePTFE), polyurethane, fluorinated ethylene propylene (FEP), silicone, polyurethane-acrylate, silicone-acrylate, urethane-silicone, and the like. Combinations of these polymers may also be used. Furthermore, different portions of the hollow tubular elongate structure 104 may also be coated with different polymers. Still furthermore, depending on the application, one or more sections of the covering 126 may be, for example, slightly porous, highly porous, or non-porous.

The covering 126 may be formed along inner and/or outer surfaces of the hollow tubular elongate structure 104. As shown, the covering 126 may extend across each of the plurality of open cells 124 in the stent body 102. In some embodiments, the covering 126 may be formed over just one or more portions of the stent body 102. For example, to allow for tissue ingrowth with the stent 100, the covering 126 may not be formed over a lumen anchoring flange 128 extending from the first end 110 and/or the second end 112. The lumen anchoring flange 128 may be a section of the hollow tubular elongate structure 104 provided to prevent migration of the stent 100 within the GI tract, while still allowing the stent 100 to be later removed. In various embodiments, the covering 126 may be applied to the hollow tubular elongate structure 104 before and/or after the control region 118 is thermally treated. It is understood that the lumen anchoring flange 128 may be included on one of the first and second ends 110, 112 of the stent body 102, or on both of the first and second ends 110, 112. In some embodiments, the stent body 102 may not include any lumen anchoring flange 128.

Figure 2:
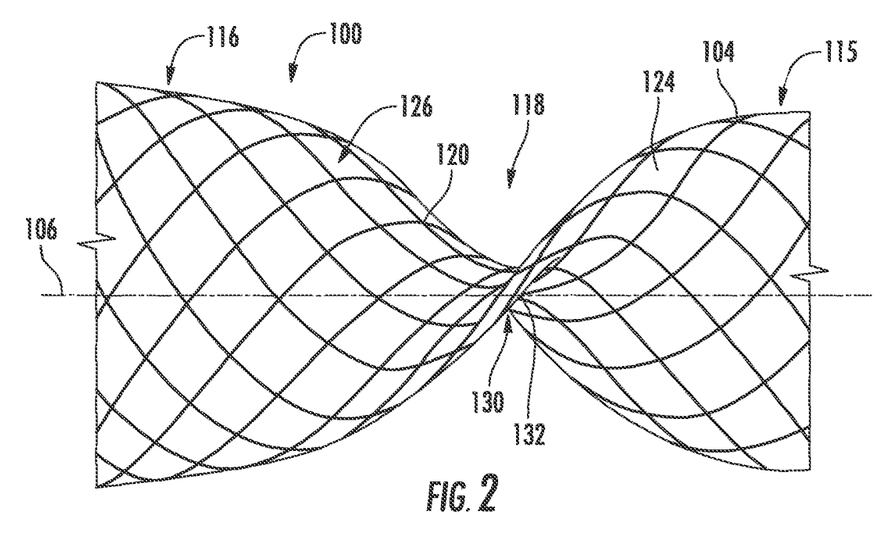
FIG. 2 is a side perspective view of a control region of the stent of FIG. 1 according to embodiments of the present disclosure.

Turning now to FIG. 2, the control region 118 of the stent 100 according to embodiments of the present disclosure will be described in greater detail. As shown, the control region 118 may include one or more constriction points 130 of the hollow tubular elongate structure 104. At the constriction point 130, the hollow tubular elongate structure 104 may be twisted about the central axis 106 to form a barrier 132 between the first and second portions 115, 116. In some embodiments, the second portion 116 may be rotated about the central axis 106, for example, by approximately 360 degrees. In other embodiments, the second portion 116 may be rotated about the central axis 106 by 90, 180, 270-720 degrees, etc. The barrier 132 may prevent matter (e.g., stool) from being delivered from an interior of the first portion 115 to an interior of the second portion 116. In some embodiments, the hollow tubular elongate structure 104 of the control region 118 may be twisted and then heat-set to establish the twisted configuration of the barrier 132.

The hollow tubular elongate structure 104 at the constriction point 130 may remain closed until a threshold pressure at the constriction point 130 causes the hollow tubular elongate structure 104 to untwist and expand radially away from the central axis 106. It will be appreciated that various properties of the hollow tubular elongate structure 104 may be varied to increase or decrease the threshold pressure necessary to open the hollow tubular elongate structure 104 at the constriction point 130. For example, a thickness of the plurality of frame members 120 in the control region 118 may be greater than a thickness of the plurality of frame members 120 of the first portion 115 and/or the second portion 116. Alternatively, or additionally, an amount of twist or rotation at the constriction point 130 may be altered. Furthermore, a stiffness of the hollow tubular elongate structure 104 at the constriction point 130 may be greater or lesser than a stiffness of the first portion 115 and/or the second portion 116. Thermal properties of the heat-set process may also be modified to alter performance of the hollow tubular elongate structure 104 at the constriction point 130.

Figure 3:
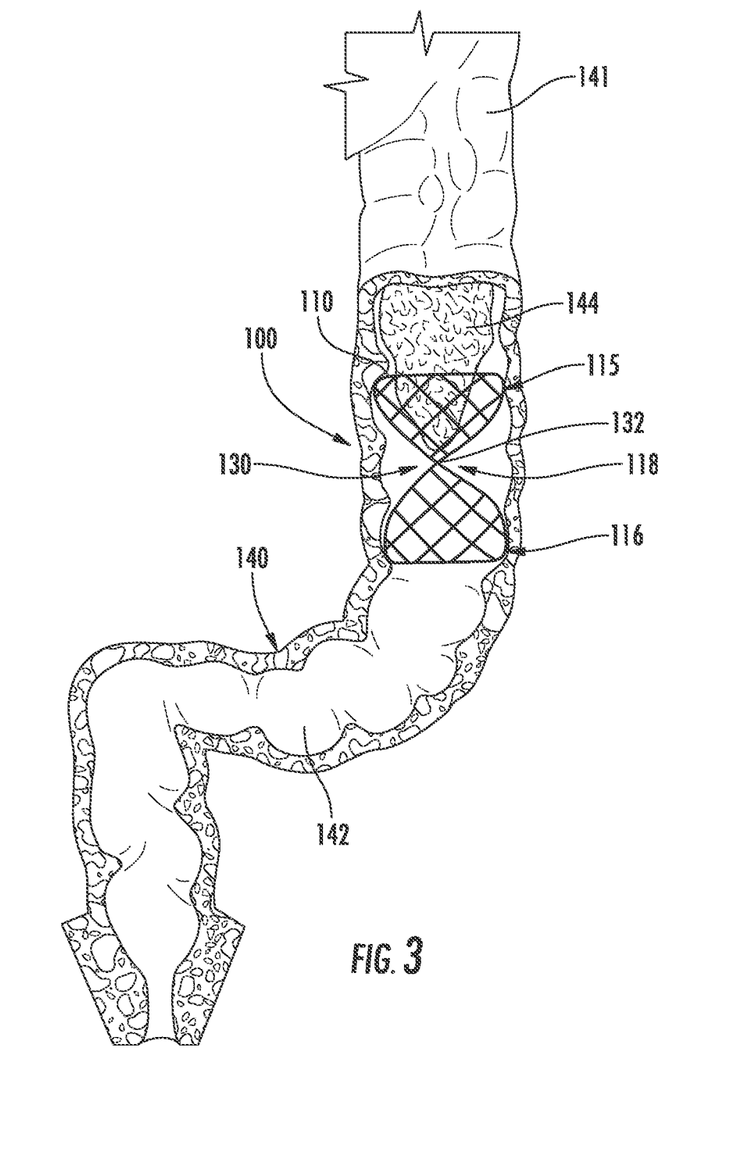
FIGS. 3-4 depict the stent of FIG. 1 positioned within a gastrointestinal tract according to embodiments of the present disclosure.
Figure 4:
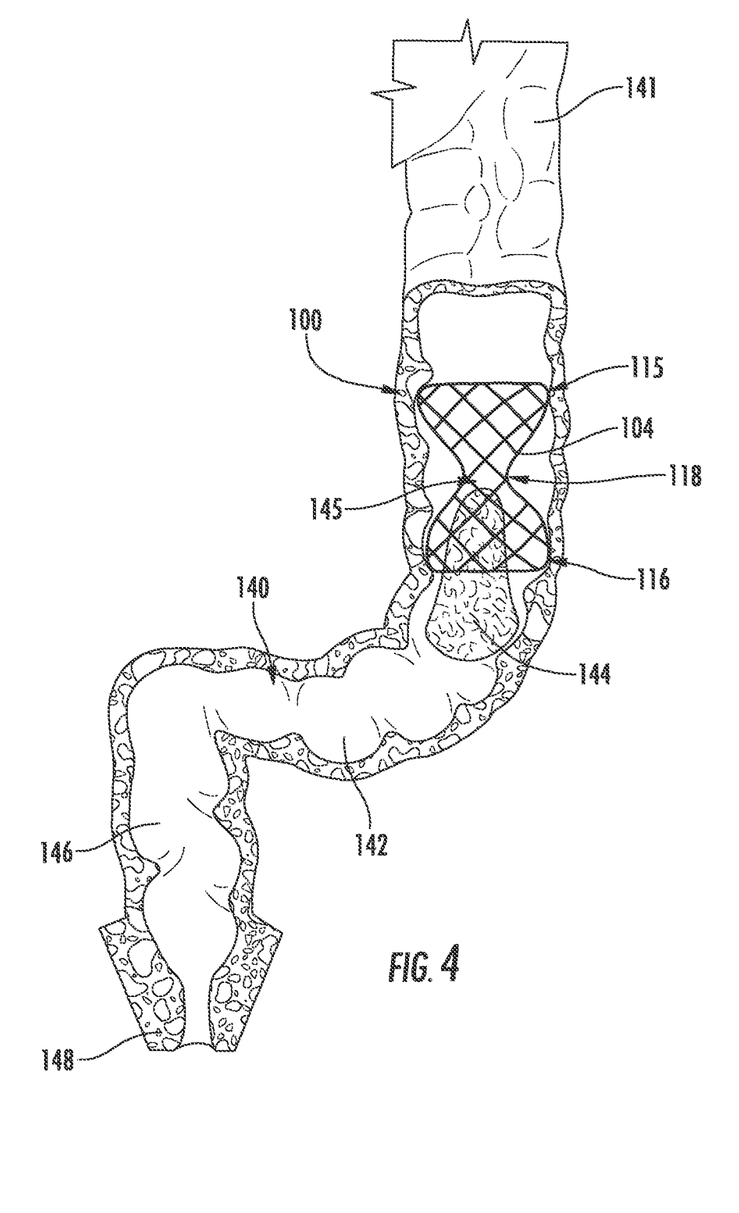

Turning now to FIGS. 3-4, operation of the stent 100 will be described in greater detail. As shown, the stent 100 may be inserted into a GI tract 140 of a patient, for example, between a descending colon 141 and a sigmoid colon 142 of a large intestine. The stent 100 may be delivered and deployed using any variety of deployment devices. For example, the stent 100 may be delivered using a coaxial delivery system including an inner and outer member assembly. The stent 100 may be constrained within an outer tube of the outer member assembly, and then deployed by pulling the outer e-tube back to expose and release the stent 100. In a deployed configuration, the first and second portions 115, 116 may expand to contact the inner surface of the body lumen, e.g., the GI tract.

As shown in FIG. 3, the stent 100 may include the barrier 132 at the constriction point 130, between the first portion 115 and the second portion 116. Stool 144 delivered from the descending colon 141 may enter the first portion 115 through the first end 110 of the stent 100, which is open. Because the barrier 132 is closed, the stool 144 is prevented from continuing into the second portion 116. Once enough of the stool 144 has built up within the first portion 115, the patient may receive a prompt, via abdominal sensation, indicating an imminent passage of the stool 144. During this initial period of time, the control region 118 of the stent 100 may remain in the closed configuration shown in FIG. 3 to provide the patient with an opportunity to reach a bathroom.

As shown in FIG. 4, the control region 118 of the stent 100 may then untwist and expand in response to a force (e.g., pressure as a result of the stool 144) upon the hollow tubular elongate structure 104 of the control region 118, thus providing a passageway 145 between the first portion 115 and the second portion 116. The first end 110 of the stent 100 may be fixed in place within the GI tract 140. In some embodiments, untwisting in the control region 118 may cause the second portion 116 to rotate (e.g., about the central axis 106 of FIG. 1), for example, more than 180 degrees relative to the first portion 115. In other embodiments, the second portion 116 may rotate approximately 360 degrees relative to the first portion 115 when in the second, open configuration. The stool 144 may then be permitted to travel through the hollow tubular elongate body down into the second portion 116 and out the open second end 112 of the stent 100 for expulsion through a rectum 146 and anus 148 of the GI tract 140. In some embodiments, the control region 118 may generally conform to the profile of the stool 144, opening only an amount to allow the stool 144 to pass therethrough, in a controlled manner. Once the stool 144 exits the second end 112 of the stent 100, which is open, the second portion 116 and the control region 118 may again twist, returning to the first, closed configuration.

Figure 5:
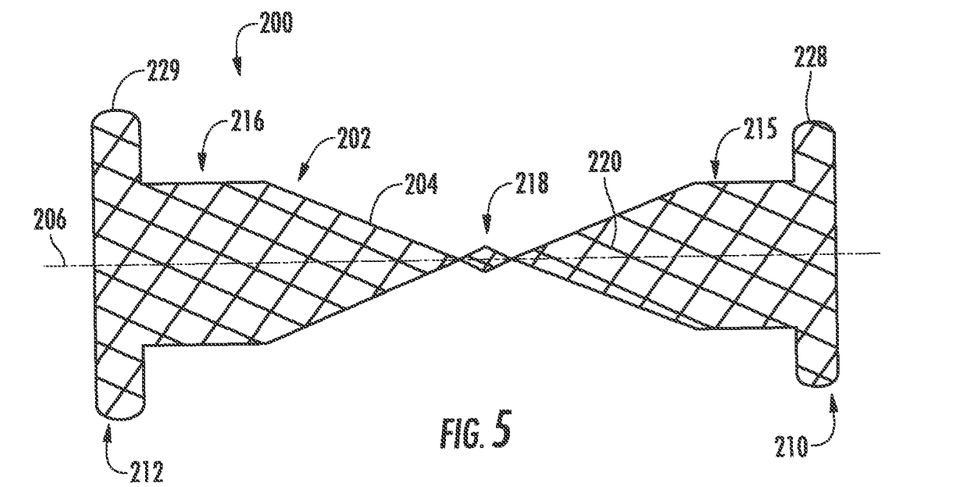
FIG. 5 is a side cross-sectional view of a stent according to embodiments of the present disclosure.
Figure 6:
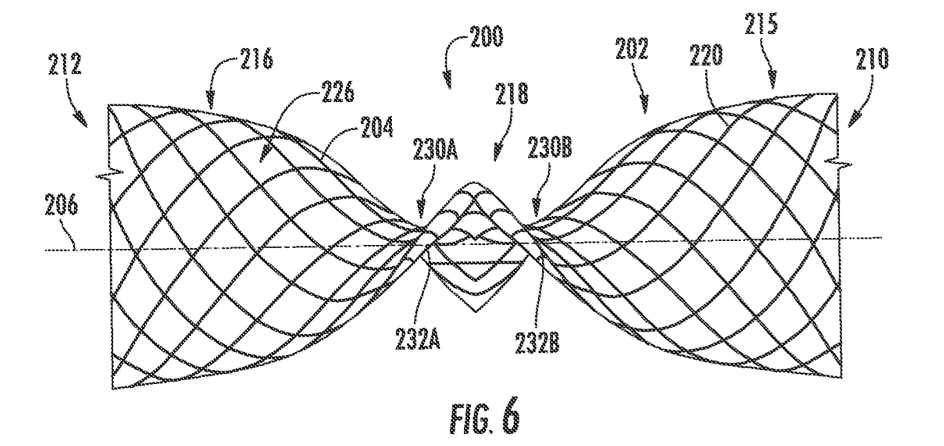
FIG. 6 is a side perspective view of a control region of the stent of FIG. 5 according to embodiments of the present disclosure.

Turning now to FIGS. 5-6, a stent 200 according to embodiments of the disclosure will be described in greater detail. As shown, the stent 200 includes many of the features previously described in relation to the stent 100 of FIGS. 1-4. Accordingly, just certain aspects of the stent 200 will hereinafter be described for the sake of brevity.

As shown, the stent 200 may have a stent body 202 defined by a hollow tubular elongate structure 204 extending along a central axis 206, between a first end 210 and a second end 212. In some embodiments, the first end 210 and the second end 212 may be open. As shown, the stent body 202 may include a first portion 215 and a second portion 216 connected to one another at a control region 218. The stent body 202 may further include a first lumen anchoring flange 228 extending from the first end 210 and a second lumen anchoring flange 229 extending from the second end 212. The first and second lumen anchoring flanges 228, 229 may be provided to prevent migration of the stent 200 within a GI tract, while still allowing the stent 200 to be later removed. For example, the first and second lumen anchoring flanges may be uncovered to allow for tissue ingrowth therewith. As will be described in greater detail below, the control region 218 may operate between a first configuration in which the hollow tubular elongate structure 204 of the control region 218 is in a closed, twisted form, and a second configuration in which the hollow tubular elongate structure 204 of the control region 218 is in an open, untwisted form.

As shown, the hollow tubular elongate structure 204 of the stent body 202 may include a plurality of frame members 220 surrounding an interior of the stent 200. The plurality of frame members 220 may be made of an elastic material, such as shape-memory wire, stainless steel, Nitinol, cobalt alloys, and/or other materials. Although non-limiting, the hollow tubular elongate structure 204 may be laser cut, woven, braided, bent, twisted, knotted, molded, tied, and/or wrapped from one or several filaments into a desired configuration. In some embodiments, the control region 218 may be twisted and then thermally treated to heat-set the hollow tubular elongate structure 204 into the configuration shown. In some embodiments, a thickness of one or more of the plurality of frame members 220 may vary. For example, a wire diameter of one or more of the plurality of frame members 220 in the control region 218 may vary relative to other wire diameters of the hollow tubular elongate structure 204 to modify the pressure at which the hollow tubular elongate structure 204 of the control region 218 changes between the open and closed configurations.

As shown, the stent 200 may include a covering 226 (e.g., silicone) over the hollow tubular elongate structure 204. The covering 226 may be formed along inner and/or outer surfaces of the hollow tubular elongate structure. In some embodiments, the covering 226 may be formed over just one or more portions of the stent body 202. For example, to allow for tissue ingrowth with the stent 200, the covering 226 may not be formed over the first lumen anchoring flange 228 and the second lumen anchoring flange 229. In various embodiments, the covering 226 may be applied to the hollow tubular elongate structure 204 before and/or after the control region 218 is thermally treated.

Turning now to FIG. 6, the control region 218 of the stent 200 according to embodiments of the present disclosure will be described in greater detail. As shown, the control region 218 may include multiple constriction points 230A-230B along the hollow tubular elongate structure 204. At each constriction point 230A-230B, the hollow tubular elongate structure 204 may be twisted about the central axis 206 to form respective barriers 232A-232B. The barriers 232A-232B may prevent matter (e.g., stool) from being delivered from an interior of the first portion 215 to an interior of the second portion 216. In some embodiments, the hollow tubular elongate structure 204 of the control region 218 is twisted and then heat-set to a desired shape to form the barriers 232A-232B at each respective constriction point 230A-230B.

The double twist configuration provided by the multiple constriction points 230A-230B in the control region 218 allows all untwisting/rotation to occur in the control region 218. Rotation of the first or second portion 215, 216, e.g., at the first or second end 210, 212, may be eliminated or reduced, thus allowing for the second lumen anchoring flange 229 (FIG. 5) to be secured in place within a GI tract of the patient. The first lumen anchoring flange 228 (FIG. 5) may also be secured in place within the GI tract of the patient. In some embodiments, the stent 200 can be heat-set with a twist (e.g., 180-360 degrees) in a first direction about the central axis 206 to form construction point 230A, followed by another 180-degree twist (e.g., 180-360 degrees) in an opposite direction about the central axis 206 to form constriction point 230B.

During operation, stool may enter the first portion 215 of the stent 200 through the first end 210. Because the barriers 232 are closed, the stool is initially prevented from continuing into the second portion 216. Said differently, the hollow tubular elongate structure 204 at the constriction points 230A-230B may remain in a closed configuration until a threshold pressure in the control region 218 causes the barriers 232A-232B of the hollow tubular elongate structure 204 to untwist and open. It will be appreciated that various properties of the hollow tubular elongate structure 204 and/or the thermal treatment may be varied to increase or decrease the threshold pressure required to open the hollow tubular elongate structure 204 at the constriction points 230A-230B. Once enough stool has built up within the first portion 215, the patient may receive a prompt, via abdominal sensation, indicating an imminent passage of the stool. During this time, the control region 218 of the stent 200 may remain in the closed configuration shown.

The control region 218 of the stent 200 may then untwist and expand in response to a force upon the hollow tubular elongate structure 204 of the control region 218, thus providing a passageway between the first portion 215 and the second portion 216. For example, the hollow tubular elongate structure 204 at both constriction points 230A-230B may untwist, in opposite directions, permitting the stool to travel through the hollow tubular elongate body and down into the second portion 216 and out the second end 212 of the stent 200. In some embodiments, the control region 218 may generally conform to the profile of the stool, opening only an adequate amount to allow the stool to pass therethrough in a controlled manner. Once the stool exits the stent 200, the control region 218 may return to the first, closed configuration wherein the hollow tubular elongate structure 204 at both constriction points 230A-230B is twisted about the central axis 206.

Figure 7:
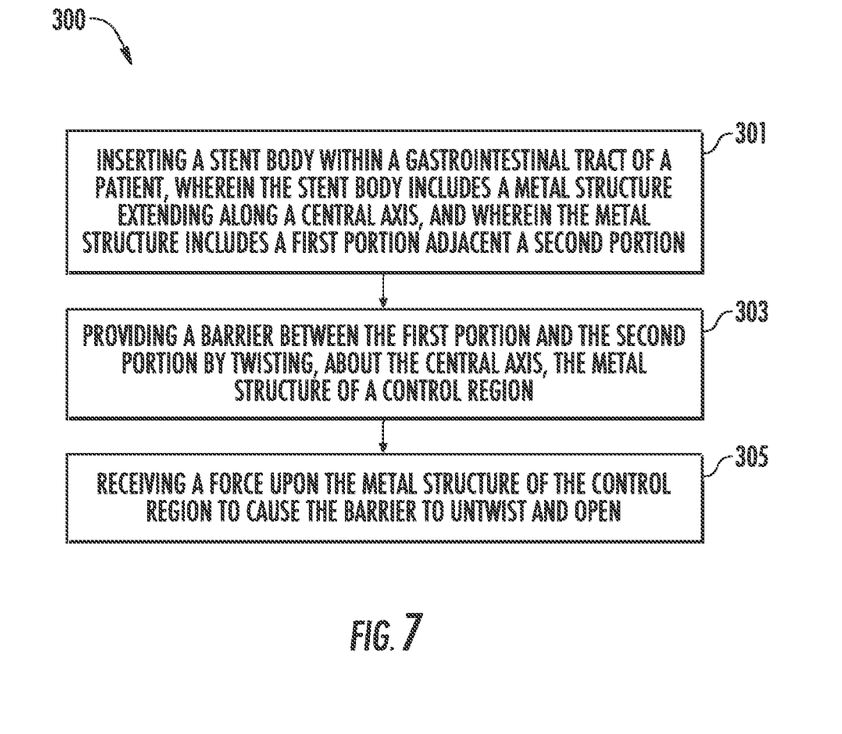
FIG. 7 is a flow diagram of a method according to embodiments of the present disclosure.

FIG. 7 is a flow diagram of a method 300 according to embodiments of the present disclosure. At block 301, the method 300 may include inserting a stent body within a gastrointestinal tract of a patient, wherein the stent body includes a hollow tubular elongate structure extending along a central axis, and wherein the hollow tubular elongate structure includes a first portion adjacent a second portion. In some embodiments, the stent body is inserted within a colon of the patient. In some embodiments, the stent body is secured within the GI tract using a lumen anchoring flange extending from at least one of the first portion and the second portion. In some embodiments, mucosal abrasion of the insertion site within the GI tract is used to encourage tissue ingrowth in the anchoring flange or another region or rim of the stent body (preferably at an end of the stent body) to mitigate migration of the stent body. In some embodiments, a covering is formed over the hollow tubular elongate structure of the stent body. In some embodiments, the covering is not provided over the anchoring flange (or other region or rim of the stent intended for mitigating migration of the stent body).

At block 303, the method 300 may include providing a barrier between the first portion and the second portion by twisting, about the central axis, the hollow tubular elongate structure of a control region. In some embodiments, the barrier is operable to untwist in response to a force upon the hollow tubular elongate structure of the control region to provide a passageway between the first portion and the second portion. The force may be provided from a buildup of stool against the barrier. In some embodiments, providing a barrier includes forming one or more constriction points in the hollow tubular elongate structure of the control region, and thermally treating the one or more constriction points.

At block 305, the method 300 includes receiving the force upon the hollow tubular elongate structure of the control region to cause the barrier to untwist and open. In some embodiments, various properties of the hollow tubular elongate structure in the control region may be varied to increase or decrease a threshold pressure necessary to open the barrier. In some embodiments, a thickness of one or more frame members in the control region may be greater than a thickness of one or more frame members of the first portion and/or the second portion. In some embodiments, an amount of twist or rotation of the barrier may be altered. Furthermore, a stiffness of the hollow tubular elongate structure in the control region may be greater or lesser than a stiffness of the hollow tubular elongate structure of first portion and/or the second portion. Still furthermore, in some embodiments, thermal properties of a heat-set process to form the barrier may be modified to alter performance of the hollow tubular elongate structure of the barrier.

Figure 8:
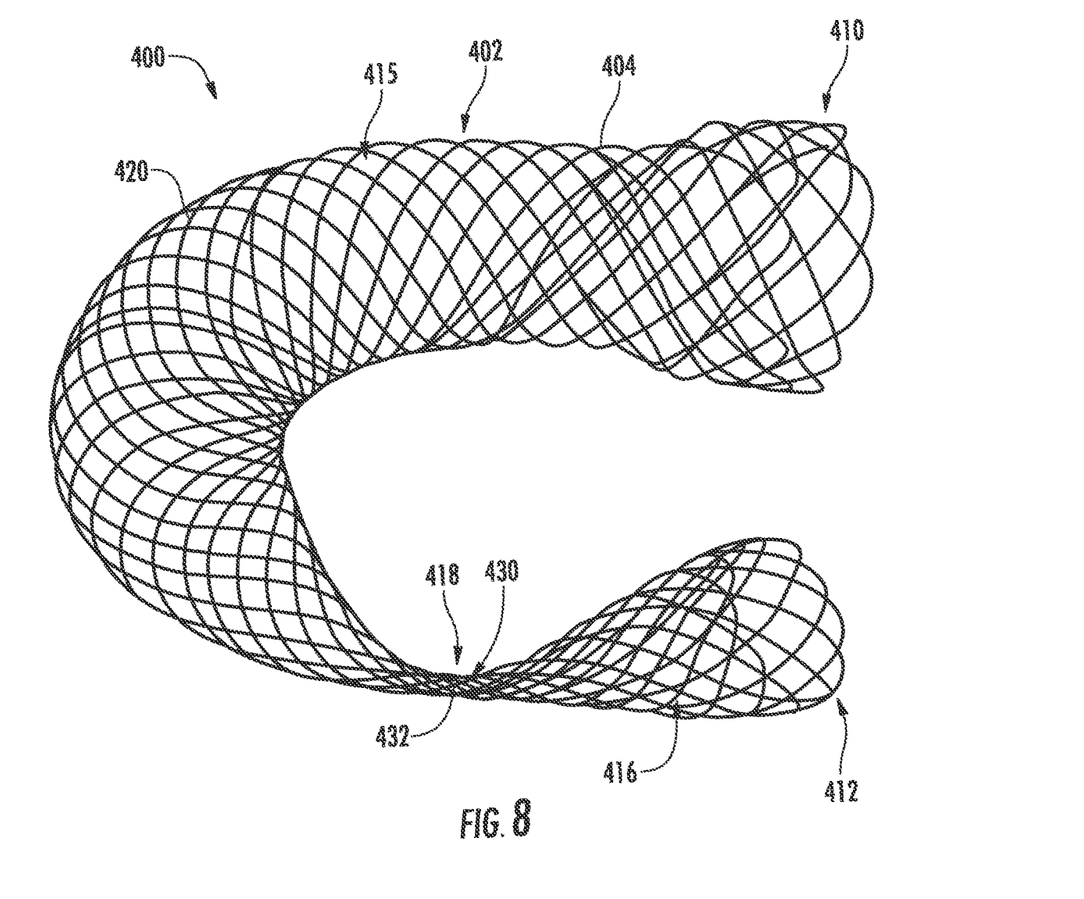
FIG. 8 is a side perspective view of a stent according to embodiments of the present disclosure.

Turning now to FIG. 8, a stent 400 according to embodiments of the disclosure will be described in greater detail. As shown, the stent 400 includes many of the features previously described in relation to the stents 100 and 200 described above. Accordingly, just certain aspects of the stent 400 will hereinafter be described for the sake of brevity.

As shown, the stent 400 may have a stent body 402 defined by a hollow tubular elongate structure 404 extending between a first end 410 and a second end 412. In some embodiments, the first end 410 and the second end 412 may be open to allow stool to enter and exit the stent body 402. As shown, the stent body 402 may include a first portion 415 and a second portion 416 connected to one another at a control region 418. In this embodiment, the stent body 402 may be bent such that the first portion 415 may generally extend within a sigmoid colon of a patient's GI tract, while the second portion 416 may be positioned within the patient's rectum. As shown, the first end 410 and the second end 412 are capable of being proximately positioned such that the first portion 415 and the second portion 416 extend generally parallel to one another. When inserted within the patent, however, the first and second portions 415, 416 may extend generally perpendicular to or colinear with each other.

As shown, the hollow tubular elongate structure 404 of the stent body 402 may include a plurality of frame members 420 surrounding an interior of the stent 400. In some embodiments, the control region 418 may be twisted and then thermally treated to heat-set the hollow tubular elongate structure 404. In some embodiments, the stent 400 may include a covering (not shown), such as a layer of silicone, formed over the hollow tubular elongate structure 404.

Similar to embodiments described above, the control region 418 may operate between a first configuration in which the hollow tubular elongate structure 404 of the control region 418 is in a closed, twisted form, and a second configuration in which the hollow tubular elongate structure 404 of the control region 418 is in an open, expanded form. In the first configuration, a barrier 432 may be formed at a constriction point 430. In the second configuration, stool may pass through the stent 400, exiting through the second end 412.

In sum, embodiments herein provide a coated stent including a twisted, shape memory control region operable to control the movement of feces and stop the flow of loose stools through to the rectum and anus. Patient discomfort and quality of life can therefore be improved using the stents and methods disclosed herein.

As used herein, the singular forms "a," "an," and "the" are intended to include the plural forms as well, unless the context clearly indicates otherwise. It will be further understood that the terms "comprises" and/or "comprising," or "includes" and/or "including" when used herein, specify the presence of stated features, regions, steps elements and/or components, but do not preclude the presence or addition of one or more other features, regions, integers, steps, operations, elements, components and/or groups thereof.

Furthermore, the terms "substantial" or "substantially," as well as the terms "approximate" or "approximately," can be used interchangeably in some embodiments, and can be described using any relative measures acceptable by one of skill. For example, these terms can serve as a comparison to a reference parameter, to indicate a deviation that will still provide the intended function. Although non-limiting, the deviation from the reference parameter can be, for example, in an amount of less than 1%, less than 3%, less than 5%, less than 10%, less than 15%, less than 20%, and so on.

The phrases "at least one", "one or more", and "and/or", as used herein, are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together.

All directional references (e.g., proximal, distal, upper, lower, upward, downward, left, right, lateral, longitudinal, front, back, top, bottom, above, below, vertical, horizontal, radial, axial, clockwise, and counterclockwise) are only used for identification purposes to aid the reader's understanding of the present disclosure, and do not create limitations, particularly as to the position, orientation, or use of this disclosure. Connection references (e.g., attached, coupled, connected, and joined) are to be construed broadly and may include intermediate members between a collection of elements and relative movement between elements unless otherwise indicated. As such, connection references do not necessarily infer that two elements are directly connected and in fixed relation to each other.

Furthermore, identification references (e.g., primary, secondary, first, second, third, fourth, etc.) are not intended to connote importance or priority, but are used to distinguish one feature from another. The drawings are for purposes of illustration only and the dimensions, positions, order and relative sizes reflected in the drawings attached hereto may vary.

Although specific embodiments have been illustrated and described herein, it should be appreciated that any arrangement calculated to achieve the same purpose may be substituted for the specific embodiments shown. This disclosure is intended to cover any and all adaptations or variations of various embodiments. It is to be understood that the above description has been made in an illustrative fashion, and not a restrictive one. Combinations of the above embodiments, and other embodiments not specifically described herein will be apparent to those of skill in the art upon reviewing the above description. Thus, the scope of various embodiments includes any other applications in which the above compositions, structures, and methods are used.

Still furthermore, although the illustrative method 300 is described above as a series of acts or events, the present disclosure is not limited by the illustrated ordering of such acts or events unless specifically stated. For example, some acts may occur in different orders and/or concurrently with other acts or events apart from those illustrated and/or described herein, in accordance with the disclosure. In addition, not all illustrated acts or events may be required to implement a methodology in accordance with the present disclosure.

Although the subject matter has been described in language specific to structural components, features, and/or methodological acts, it is to be understood that the subject matter defined in the appended claims is not necessarily limited to the specific components, features, and/or acts described above. Rather, the specific features and acts described above are disclosed as example forms of implementing the claims.

What is claimed is:

1. A medical stent, comprising:
   a stent body defined by a hollow tubular elongate structure extending along a central axis, the stent body including a first portion and a second portion; and
   a control region between the first portion and the second portion;
   wherein:
   the control region comprises a first constriction point and a second constriction point adjacent the first constriction point;
   the hollow tubular elongate structure at each of the first and the second constriction points is substantially closed;
   in a first configuration, the control region is in a closed, twisted configuration; and
   in a second configuration, the control region untwists relative to the first portion and the second portion, in response to a threshold pressure when deployed in a patient's body, into an open, expanded configuration allowing passage of materials through the stent body.

2. The medical stent of claim 1, wherein the control region is connected at a first end to the first portion and at a second end to the second portion.

3. The medical stent of claim 1, further comprising a covering formed along the hollow tubular elongate structure.

4. The medical stent of claim 3, wherein the covering is made from silicone.

5. The medical stent of claim 1, wherein in the first configuration, the second portion is rotated more than 180 degrees relative to the first portion.

6. The medical stent of claim 1, wherein in the first configuration the hollow tubular elongate structure of the control region is rotated about the central axis by approximately 360 degrees.

7. The medical stent of claim 1, wherein at the first constriction point the hollow tubular elongate structure of the control region is rotated in a first direction about the central axis by 180 degrees, and wherein at the second constriction point the hollow tubular elongate structure of the control region is rotated in a second direction about the central axis by 180 degrees.

8. The medical stent of claim 1, the stent body further comprising a lumen anchoring flange extending from at least one of: the first portion and the second portion.

9. The medical stent of claim 1, wherein the first portion includes a first open end, and wherein the second portion includes a second open end.

10. The medical stent of claim 1, wherein in the second configuration the second portion is rotated at least 180 degrees relative to the first portion.

11. The medical stent of claim 1, wherein the first constriction point forms a barrier in the control region.

12. A medical stent, comprising:
    a stent body defined by a hollow tubular elongate structure extending along a central axis, the stent body including a first portion and a second portion; and
    a control region between the first portion and the second portion;
    wherein:
    the control region comprises a first constriction point and a second constriction point adjacent the first constriction point;
    the hollow tubular elongate structure at the first constriction point is rotated with respect to the first portion of the stent body and about the central axis in a first direction;
    the hollow tubular elongate structure at the second constriction point is rotated with respect to the first constriction point and about the central axis in a second direction opposite the first direction;
    in a first configuration, the control region is in a closed, twisted configuration; and
    in a second configuration, the control region untwists relative to the first portion and the second portion, in response to a threshold pressure when deployed in a patient's body, into an open, expanded configuration allowing passage of materials through the stent body.

13. The medical stent of claim 12, wherein the control region is connected at a first end to the first portion and at a second end to the second portion.

14. The medical stent of claim 12, further comprising a covering formed along the hollow tubular elongate structure.

15. The medical stent of claim 14, wherein the covering is made of silicone.

16. The medical stent of claim 12, wherein in the first configuration, the second portion is rotated more than 180 degrees relative to the first portion.

17. The medical stent of claim 12, wherein in the first configuration the hollow tubular elongate structure of the control region is rotated about the central axis by approximately 360 degrees.

18. The medical stent of claim 12, wherein at the first constriction point the hollow tubular elongate structure of the control region is rotated in the first direction about the central axis by 180 degrees, and wherein at the second constriction point the hollow tubular elongate structure of the control region is rotated in the second direction about the central axis by 180 degrees.

19. The medical stent of claim 12, wherein in the second configuration the second portion is rotated at least 180 degrees relative to the first portion.

20. The medical stent of claim 12, wherein the first constriction point forms a barrier in the control region.

* * * * *